United States Patent [19]

Toth

[11] Patent Number: 4,472,420

[45] Date of Patent: Sep. 18, 1984

[54] METHOD FOR TREATMENT OF SHOCK

[75] Inventor: Phillip D. Toth, Lebanon, Ind.

[73] Assignee: Methodist Hospital of Indiana, Inc., Indianapolis, Ind.

[21] Appl. No.: 524,457

[22] Filed: Aug. 18, 1983

[51] Int. Cl.³ ............................................ A61K 31/42
[52] U.S. Cl. .................................................. 424/272
[58] Field of Search ........................................ 424/272

[56] References Cited

U.S. PATENT DOCUMENTS 4,355,029 10/1982 Ridolfo .............................. 424/232

Primary Examiner—Stanley J. Friedman
Attorney, Agent, or Firm—Woodard, Weikart, Emhardt & Naughton

[57] ABSTRACT

A method for the treatment of shock is disclosed which includes the administration of a therapeutically effective amount of benoxaprofen, which may be administered either as a pretreatment or subsequent to the onset of the shock condition. The benoxaprofen is preferably administered intravenously.

14 Claims, No Drawings

METHOD FOR TREATMENT OF SHOCK

BACKGROUND OF THE INVENTION

1. Field of the Invention

The present invention relates to the field of methods for the treatment of shock, and more particularly to a method for treating shock by use of drugs.

2. Description of the Prior Art

The term shock is applied to a variety of pathophysiological conditions associated with hypotension. Shock is a condition of acute peripheral circulatory failure due to derangement of circulatory control or loss of circulating fluid and is marked by pallor and claminess of the skin, decreased blood pressure, feeble rapid pulse, decreased respiration, restlessness, anxiety, and sometimes unconsciousness. Some examples are hemorrhagic shock (blood loss), cardiogenic shock (heart attack), and septic shock (infection).

In spite of aggressive therapy, the morbidity and mortality rate for shock patients are quite high, in the range of 20–70%. Moreover, this has been a condition which has been extremely difficult to treat. Much research has been conducted in this field in an effort to determine the mechanism of the shock condition and methodologies for satisfactory treatment of shock after its onset.

There has been recent speculation that the body releases certain hormones or mediators which cause the low blood pressure. Many vasoactive mediators have been implicated in the pathophysiology of many shock states including endotoxic shock. The mediators which have received much attention in endotoxic shock have been the opioids, prostanoids, histamine, kinins, serotonin, VIP, etc. However, what has yet to be established is the relative hemodynamic contribution of each of these mediators in a given shock model.

Some drugs are currently being promoted for use in the treatment of shock. Previously, the use of a massive dose of glucocorticoids in a patient with septic shock was being employed. The Food and Drug Administration recently reviewed the indications for the use of corticosteroids in septic shock, in particular for a drug methylprednisolone sodium succinate, and decided to remove septic shock from the product insert as an indication for the use of high doses. The use of this and related drugs for the treatment of shock is discussed in an article entitled "Septic Shock and Corticosteroids," John N. Sheagren, M.D., appearing in The New England Journal of Medicine, pp. 456–7, Aug. 20, 1981.

It has previously been demonstrated that the cyclooxygenase inhibitor, ibuprofen, given 60 minutes after endotoxin administration could improve hemodynamics but not survival over control animals in a canine endotoxic shock model. A paper on this subject entitled "The Effects of Different Vasoactive Mediator Antagonists on Endotoxic Shock in Dogs I" was presented at the Fifth Annual Conference on Shock, at Smugglers' Notch, Vermont on June 9–11, 1982.

A method for the treatment of shock is described in U.S. Pat. No. 4,267,182, issued to Holaday on May 12, 1981. This method includes the administration to the patient of any of a number of drugs including naloxone, naltrexone, nalorphine, diprenorphine, levallorphan, pentazocine, metazocine, cyclazocine, etazocine and the acid addition salts thereof. Each of these drugs is indicated as a narcotic antagonist drug.

The present invention relates to the use of benoxaprofen for the treatment of shock. Benoxaprofen is a known anti-inflammatory drug which has been available from Eli Lilly & Co. of Indianapolis, Indiana for use in the treatment of arthritis. The therapeutic method for treating rheumatoid arthritis by the administration of benoxaprofen and aspirin is disclosed in U.S. Pat. No. 4,355,029, issued to Ridolfo on Oct. 19, 1982. Other anti-inflammatory drugs and their use are described in U.S. Pat. Nos. 4,282,214, issued to Flora on Aug. 4, 1981; 4,185,100, issued to Marvel on Jan. 22, 1980; 4,142,054, issued to Amin on Feb. 27, 1979; 4,135,051, issued to Walker on Jan. 16, 1979; and 4,107,439, issued to Salmond on Aug. 15, 1978.

Despite the research conducted in this field, there has remained a strong need for a method for the treatment of shock to both improve hemodynamics and survival. Although various drugs have been investigated for this purpose, the results to date have not been highly successful.

SUMMARY OF THE INVENTION

Briefly describing one aspect of the present invention there is provided a method for the treatment of shock which includes administering to the patient a therapeutically effective amount of benoxaprofen or fenoprofen.

It is an object of the present invention to provide a method for the treatment of shock.

It is a further object of the present invention to provide a method for treating shock which is successful both in improving hemodynamics and in overall recovery from the condition.

Another object of the present invention is to provide a method of treating shock which is readily followed.

A further object of the present invention is to provide a method for the treatment of shock either by pre-treatment or by treatment late in the condition.

Further objects and advantages of the present invention will become apparent from the description of the preferred embodiment which follows.

DESCRIPTION OF THE PREFERRED EMBODIMENT

For the purposes of promoting an understanding of the principles of the invention, reference will now be made to the preferred embodiment and specific language will be used to describe the same. It will nevertheless be understood that no limitation of the scope of the invention is thereby intended, such alterations and further modifications in the described process, and such further applications of the principles of the invention as illustrated therein being contemplated as would normally occur to one skilled in the art to which the invention relates.

The present invention involves the treatment of shock by the administration of benoxaprofen or fenoprofen in a therapeutically effective amount. As will be indicated in the specific examples to follow, it has been found that the administration of such drugs has resulted in both improved hemodynamics and increased survival. These results evidence a remarkable impact of the use of these drugs in the treatment of a condition which has been a severe problem.

Benoxaprofen and fenoprofen are drugs which are known in the industry and in the past have been indicated primarily for their efficacy as anti-inflammatories. These drugs consequently have been available to the field in varying administration forms and dosages, and the preparation of such is therefore not considered necessary in this description relating to a use for such drugs. It is noted that these drugs are readily soluble, and their preparation in IV form is therefore easily accomplished by usual techniques known to persons skilled in the art.

It is interesting to note the currently perceived mechanism associated at least in part with the shock condition. Although not intended in any way as a limitation of the present invention, the potential relationship between the operation of the benoxaprofen or fenoprofen will be discussed.

There is a recognized mechanism known as the protaglandin cascade or arachidonic acid cascade which leads to the release of several different compounds within the body. This cascade begins with the presence of inaccessible phospholipids within the body. Upon stimulus, these phospholipids convert to a form in which they are accessible, and such conversion is believed to be inhibited by glucocorticoids. Thus, certain glucocorticoids have been investigated for counteracting the development of this cascade, although with doubtful success as indicated earlier.

The accessible phospholipids are available to be acted upon by phospholipase for conversion into arachidonic acid. This acid in turn may yield several additional compounds along one of at least three pathways. Conversion by lipoxygenase results in the production of leukotrienes, 5,15 HPETE and 12-HPETE. Several other compounds result from the operation of cyclo-oxygenase on the arachidonic acid in the presence of oxygen to form $PGG_2$, convertible in turn to $PGH_2$, prostacyclin, thromboxane $A_2$, etc.

In the part, it has been considered to use inhibitors to the cyclo-oxygenase pathway in shock. One such example is ibuprofen, discussed earlier. However, the results have been typically reported as improving hemodynamics, but not mortality.

Benoxaprofen, which has now been found to provide superior results in treating shock, is a dual inhibitor of both the lipoxygenase and cyclo-oxygenase pathways. The use of a dual inhibitor therefore leads to improved treatment of the shock condition.

Prior studies have demonstrated in a canine endotoxic shock model ($LD_{100}$) that the selective cyclo-oxygenase inhibitor, ibuprofen, given 60 minutes after endotoxin administration, could improve hemodynamics within 30–60 minutes, but did not improve survival over control animals. Naloxone administration has demonstrated only transient hemodynamic improvement. These and other data suggest that the products of the prostaglandin cascade are probably more hemodynamically important than the opioids as vasoactive mediators in this type of canine endotoxic shock. Leukotrienes, products of the lipoxygenase pathway, have also been implicated as important vasoactive mediators in the endotoxic (septic) shock syndrome. When given systemically, they can cause hypotension, can increase vascular permeability, and can decrease myocardial contractility which are characteristic features of shock.

EXAMPLE I

A study was conducted to examine the effect of benoxaprofen, a dual lipoxygenase and cyclo-oxygenase inhibitor, in a canine endotoxic model and compare it to ibuprofen treatment. After thiopental anesthesia (30 mg/kg i.v.), animals were instrumented to measure various cardiovascular parameters.

Endotoxic shock was induced by injecting E. coli (0111:B4) endotoxin (1 mg/kg i.v.). Benoxaprofen (10 mg/kg i.v.) (n=13), ibuprofen (12.5 mg./kg) (n=6), or saline (n=12) was injected 60 minutes after endotoxin administration. During the treatment period, both benoxaprofen and ibuprofen increased mean arterial pressure, heart rate and vascular resistance to the same degree over the control animals. Benoxaprofen did increase $dp/dt_{max}$ while ibuprofen did not. Twenty-four hour survival was 0% for the control animals (n=12), 0% for the ibuprofen group (n=6) and 61.5% for the benoxaprofen group (n=13). These data indicate that benoxaprofen could improve survival in an otherwise lethal endotoxic model.

METHODS

Healthy adult male hounds weighing 20–25 kg were anesthetized with thiopental (25 mg/kg) i.v. two days prior to each experiment. They were then shaved and depilated in the neck, mid thorax, and femoral areas and allowed to spontaneously recover. On the day of the experiment, each dog was again anesthetized with thiopental (25 mg/kg i.v.), intubated with a cuffed endotracheal tube, and allowed to breath spontaneously on room air. Additional small doses of thiopental (1–2 mg/kg) were administered when necessary. On the shaved areas, the impedance electrode tape was placed circumferentially in the usual manner.

In the neck, the right jugular vein was exposed and a Swan-Ganz catheter was inserted to measure mean pulmonary artery pressure (PAP) and mean pulmonary artery wedge (PAW) pressure. Also through the same neck approach, a "pigtail" catheter was inserted into the left ventricle to measure $dP/dt_{max}$. In the left groin area, the femoral artery was exposed and a 7F catheter was inserted and connected to a transducer to measure mean arterial pressure (MAP). All pressures were measured with Gould-Statham P23Db pressure transducers which were calibrated daily.

Other cardiodynamics were measured by a Minnesota Impedance Cardiograph (Model 304B) (Surcom, Inc., Minneapolis, MN) which is a tetrapolar electrode system. The outer two leads (1 and 4) were connected to an oscillator which produced a 100 kHz, 4 ma constant current and detected an EKG signal. The inner two electrodes were connected to an Impedance Cardiograph Microcomputer (Model 7000) (Surcom, Inc., Minneapolis, MN) which measured on a beat-by-beat basis, heart rate (HR), stroke volume (SV), cardiac output (CO), and Heather Index (HI) (a measurement of contractility). It has been demonstrated in the past that CO-measured by impedance is equivalent to CO determined by the thermodilution or dye dilution methods. Recent work has demonstrated a correlation coeffient of $r = 0.88$ for SV determined by impedance and thermodilation during the pre-shock and shock periods of this $LD_{100}$ canine endotoxic shock model. Total peripheral resistance (TPR) was calculated by the following formula: TPR=MAP/CO. Ejection fraction (EF) was calculated from a standard impedance signal using the method of Judy which has been shown to be equivalent to a single-pass radionuclide or ventriculogram methods. End diastolic volume was calculated as follows: EDV=SV/EF.

All impedance data and pressures were recorded simultaneously on a Beckman Type R Dynograph. After all surgery was completed, each dog was given heparin (10,000 U i.v.). After a 30 minute baseline period, each dog was given endotoxin (1 mg/kg i.v.) (E. coli 0111:B4) (Difco).

Sixty minutes after endotoxin administration, ibuprofen (12.5 mg/kg), benoxaprofen (10 mg/kg) or an equivalent volume of saline was injected intravenously. Animals were physiologically monitored for an additional 2½ hours. The catheters were then removed, and the animals were returned to their cages. Animals were observed until death and then were autopsied.

STATISTICAL ANALYSIS

Data was analyzed using paired Student t-tests, two group Student t-tests, repeated measures analysis of variance, and Fisher's exact test. A p-value of $\leq 0.5$ was considered significant.

RESULTS

Comparison of the groups demonstrated (n=12) no significant differences for any of the parameters during the baseline and the shock periods. No hemodynamic changes were noted when the drugs were administered to instrumented non-shocked animals. At time 0, endotoxic shock was induced by injecting endotoxin (E. coli 0111:B4) (1 mg./kg i.v.). Sixty minutes after endotoxin administration, the drugs or an equivalent volume of saline was administered.

The typical hemodynamic profile after endotoxin administration consisted of essentially three phases: (1) early, rapid hypotension, (2) transient compensatory phase, and (3) late hypotension. Both ibuprofen and benoxaprofen were found to be equally effective in increasing MAP to near pre-shock levels. Although both increased HR, there was no improvement of CO in either group. EDV remained depressed after drug intervention in either group indicating that venous return could not account for the increase in MAP of both treatment groups. Although HI, the impedance contractility index, demonstrated no differences among the groups, dp/dt$_{max}$ was significantly improved in the benoxaprofen treated group. The parameter with the most significant change to explain the increae of MAP was TPR, which increased to the same extent in both the ibuprofen and benoxaprofen groups. PVR was improved by both ibuprofen and benoxaprofen to an equal extent. Survival at 24 hours for the ibuprofen and controls was 0% while benoxaprofen was 61.5% (8/13).

TABLE 1

| TIME | SURVIVAL | | |
|---|---|---|---|
| | BENOXAPROFEN n = 13 | IBUPROFEN n = 6 | CONTROL n = 12 |
| 24 hours | 8* | 0 | 0 |
| 2 days | 6* | 0 | 0 |
| 3 days | 3 | 0 | 0 |
| 4 days | 2$^a$ | 0 | 0 |
| 5 days | 1 | 0 | 0 |
| 6 days | 1$^a$ | 0 | 0 |

$^a$Animal Sacrificed
*p-value $\leq$ .05

EXAMPLE II

A study was designed to examine the effects of benoxaprofen given 120 minutes after endotoxin administration to determine if improvement of hemodynamics and survival could be obtained with a longer shock period. After thiopental anesthesia (30 mg/kg i.v.), the animals were instrumented to measure various cardiovascular parameters. Endotoxic shock was induced by injecting E. coli (0111:B4) endotoxin (1 mg/kg i.v.). Benoxaprofen (10 mg/kg i.v.) (n=8) or saline (n=12) was injected 120 minutes after endotoxin administration. During the treatment period, benoxaprofen demonstrated a significant and sustained improvement of mean arterial pressure, total peripheral resistance, and dp/dt$_{max}$. Survival after 24 hours for control animals was 0% (0/12) versus 50% (4/8) for the benoxaprofen group. These data indicate that even with delayed administration benoxaprofen could improve hemodynamics and survival in an otherwise lethal endotoxic shock model.

METHODS

Healthy, adult male hounds weighing 20–25 kg were prepared as described in Example I. Pulmonary vascular resistance (PRV) was calculated from the formula:

$$PVR = PAP-PAW/CO.$$

Two hours after endotoxin administration, benoxaprofen (10 mg/kg) or an equivalent volume of saline was injected intravenously. Animals were physiologically monitored for an additional 2½ hours. The catheters were then removed and animals were returned to their cages. Animals were observed every 12 hours until death and then were autopsied.

STATISTICAL ANALYSIS

Data was analyzed using paired Student t-tests, repeated analysis of variance, and Fisher's exact test. A p-value of $\leq 0.05$ was considered significant.

RESULTS

Comparison of the benoxaprofen group (n=8) and the control group (n=12) showed no significant differences among any of the parameters during the baseline and the shock periods. Although small differences were noted in the initial part of the baseline period for SV, CO, and TPR, these parameters were not statistically different just prior to endotoxin administration. At time 0, endotoxic shock was induced by injecting endotoxin. Two hours after endotoxin administration, benoxaprofen (10 mg/kg i.v.) or an equivalent volume of saline was injected. Benoxaprofen (10 mg/kg) given to instrumented, non-shocked animals had no effect on hemodynamics. A rapid improvement of MAP followed after benoxaprofen administration. However, there were no major increases of HR, SV, EDV, or CO to account for the increase of blood pressure. Although HI showed no improvement over controls, dP/dt$_{max}$ did demonstrate a significant and sustained increase over controls.

There was a very rapid and sustained increase of TPR but not PVR in the benoxaprofen group. The 24 hour survival was 50% (4/8) for the benoxaprofen animals and 0% (0/12) for the controls. Compared to controls, the benoxaprofen group demonstrated an increased survival for 3 days after treatment.

TABLE 1

| TIME | SURVIVAL | |
|---|---|---|
| | CONTROL n = 12 | 2 HOUR SHOCK n = 8 |
| 24 hours | 0 | 4* |
| 2 days | 0 | 4* |
| 3 days | 0 | 3* |
| 4 days | 0 | 1 |
| 5 days | 0 | 1 |
| 6 days | 0 | 1 |

*p $\leq$ .05

These data indicate that late (2 hours) intervention after endotoxin administration of benoxaprofen can still result in improvement of hemodynamics and survival in the lethal ($LD_{100}$) endotoxin model. The underlying mechanism for the MAP improvement was an increase of TPR which was also observed when benoxaprofen was administered after one hour of endotoxic shock. Although $dp/dt_{max}$ was increased suggesting an improvement of contractility, no increase of CO was observed. If this were an improvement of myocardial kinetics, then this "cardioprotective" effect of benoxaprofen might help to explain the increase of survival in this group.

It has been shown that the administration of a dual inhibitor not only improves hemodynamics but also could extend survival in an otherwise lethal canine endotoxic shock model. Benoxaprofen and ibuprofen had similar hemodynamic characteristics when administered one hour after endotoxin. Both increased MAP, HR and TPR to a similar extent. A major difference was that benoxaprofen improved $dp/dt_{max}$ to a greater extent than ibuprofen during the observation period.

The hemodynamic improvement caused by benoxaprofen were similar whether it was administered after 1 or 2 hours after endotoxic shock. As noted above, the increases of MAP, TPR, and $dp/dt_{max}$ were similar. Only small differences were noted when benoxaprofen was administered during the two different shock periods. After a 1 hour shock, there was an increase of HR and PVR while after a 2 hour shock, benoxaprofen demonstrated no improvement of these parameters.

Since benoxaprofen is a dual cyclo-oxygenase and lipoxygenase inhibitor, one could hypothesize that the inhibition of the products of the lipoxygenase pathway (e.g. leukotrienes) contributed to the increased survival in this model. If this is true, then other dual inhibitors should increase hemodynamics and survival as well. Benoxaprofen has also been shown to inhibit phospholipase $A_2$, an early pivotal enzyme in the prostaglandin cascade. This "steroid" effect may also help to explain its beneficial effects.

EXAMPLE III

This study examined the effects of benoxaprofen, a dual cyclo-oxygenase and lipoxygenase inhibitor, on a canine hemorrhagic shock model. After thiopental anesthesia, the animals were instrumented to measure various cardiovascular parameters. All animals were bled to and maintained at a mean arterial pressure (MAP) of 60 mmHg for 90 minutes. After the shock period, animals were then given benoxaprofen (10 mg/kg) (n=6) or an equivalent volume of saline (n=6). After another 90 minutes observation period, the shed blood was reinfused. A significant increase of MAP was noted in the benoxaprofen group secondary to an increase of total peripheral resistance (TPR).

METHODS

Healthy, adult male beagles weighing 10–15 kg were prepared in Example I. Pulmonary vascular resistance (PVR) was calculated from the formula: PVR=PAP-PAW/CO.

After a 15 minute baseline period, the animals were bled to a MAP of 60 mmHg over a 30 minute period. This pressure was maintained for another 60 minutes at this level by raising or lowering the blood bag as needed. After the 90 minutes of shock, the animals were given either benoxaprofen (10 mg/kg) (n=6) or an equal volume of saline (n=6) intravenously. After another 90 minutes observation period, the shed blood was reinfused in both groups and observed for another 45 minutes. After this last observation period, the catheters were removed, the vessels ligated, and the animals were returned to their cages. Animals were observed every 12 hours until death and then autopsied.

STATISTICAL ANALYSIS

Data was analyzed using paired Student t-tests, two group Student Fisher's exact text, and repeated measures analysis of variance. A p-value of $\leq 0.05$ was considered significant.

RESULTS

Analysis of data during the preshock and shock periods demonstrated no statistical differences ($p \leq 0.05$) between the groups. Benoxaprofen (10 mg/kg) given to instrumented, non-shocked animals had no effect on hemodynamics. There was an increase of MAP after benoxaprofen administration. There was no increase of HR, SV, CO, EDV, HI, or $dP/dt_{max}$ to account for the increase of MAP. The parameter which did increase to account for the increase of MAP was TPR. There was also a slight increase of PVR observed in the treatment group. Survival at 72 hours was 50% (3/6) in the control group and 100% (6/6) in the benoxaprofen group.

TABLE 1

| TIME | SURVIVAL | |
|---|---|---|
| | CONTROL (n = 6) | BENOXAPROFEN (n = 6) |
| 24 hours | 3 | 6 |
| 48 hours | 3 | 6 |
| 72 hours | 3 | 6 |

This study demonstrated that benoxaprofen, a dual cyclo-oxygenase and lipoxygenase inhibitor, increased MAP secondary to a rise of TPR. Fenoprofen, a more selective cyclo-oxygenase inhibitor, also has been found to increase MAP to the same extent as benoxaprofen in the same hemorrhagic shock model. This would suggest that the products of the cyclo-oxygenase pathway (e.g. $PCI_2$) may contribute more to the hypotension than the lipoxygenase products.

It has therefore been shown that the administration of benoxaprofen will effectively treat the shock condition when given in therapeutic amounts. Benoxaprofen is also appropriate for the pretreatment of patients considered to have a high risk of infection (e.g. surgery) or to prevent other types of potential shock situations. In particular, the administration of the drug desirably within an hour or two of the onset of the shock condition improves hemodynamics and increases the chances of survival from the shock condition.

The benoxaprofen may be administered in a variety of manners, typically depending on the circumstances of administration. The drug may for example be administered parenterally, and preferably intravenously.

EXAMPLE IV

A study was conducted to examine the effects of fenoprofen, a cyclo-oxygenase inhibitor, in the same canine endotoxic shock model as previously described. After pentobarbital anesthesia, the dogs were instrumented for measurement purposes and figures were calculated as described in the preceding examples. Endotoxic shock was induced by injecting E. coli (0111:B4) endotoxin (1 mg/kg i.v.). Fenoprofen (1 mg/kg i.v.) (n=5) or fenoprofen (10 mg/kg i.v. (n=6) was administered 60 minutes after endotoxin administration. Fenoprofen rapidly increased MAP to near pre-shock levels within 30-45 minutes by increasing TPR, PVR, dP/dt, and EDV in a dose response manner. Survival after 24 for the groups was 0/12 for the control, 3/5 for the 1 mg/kg group (p value versus the control being 0.015), and 4/6 for the 10 mg/kg group (p value 0.005).

What I claim is:

1. A method for the treatment of shock which comprises administering parenterally to a person suffering from shock a therapeutically effective amount of benoxaprofen.

2. The method of claim 1 in which the benoxaprofen is administered within two hours after onset of the shock condition.

3. The method of claim 1 in which the benoxaprofen is administered intravenously.

4. A method for the treatment of a person having a potential for the onset of a shock condition, which method comprises administering parenterally to the person having the potential for the onset of shock a therapeutically effective amount of benoxaprofen.

5. The method of claim 4 in which the benoxaprofen is administered to a person having a high risk of the onset of shock.

6. The method of claim 4 in which the benoxaprofen is administered to a hospitalized patient.

7. The method of claim 6 in which the patient has a high risk of the onset of shock.

8. The method of claim 4 in which the benoxaprofen is administered to a person who has recently suffered a significant loss of blood.

9. The method of claim 4 in which the benoxaprofen is administered to a person having a high risk of infection.

10. The method of claim 9 in which the person is a hospitalized patient.

11. The method of claim 4 in which the benoxaprofen is administered to a hospitalized patient prior to the patient's undergoing a surgical procedure.

12. The method of claim 11 in which the benoxaprofen is administered to the patient within an hour before the surgical procedure.

13. The method of claim 11 in which the surgical procedure subjects the patient to a high risk of infection.

14. The method of claim 11 in which the surgical procedure subjects the patient to a high risk of a significant blood loss.

* * * * *